United States Patent [19]

Van Beveren et al.

[11] Patent Number: 4,841,026

[45] Date of Patent: Jun. 20, 1989

[54] VIRALLY INACTIVATED, NON-TOXIC, HUMAN TRANSFERRIN PREPARATION

[75] Inventors: Shirley M. Van Beveren; Albert R. Pappenhagen, both of Concord, Calif.

[73] Assignee: Miles Laboratories, Inc., Elkhart, Ind.

[21] Appl. No.: 7,150

[22] Filed: Jan. 27, 1987

[51] Int. Cl.[4] .......................... C07K 15/14; C07K 3/24
[52] U.S. Cl. .................... 530/394; 530/418; 530/421; 530/380; 530/395; 435/240.3; 514/8
[58] Field of Search ................... 514/8; 530/421, 380, 530/395, 394, 400, 420, 416

[56] References Cited

U.S. PATENT DOCUMENTS

| 2,390,074 | 12/1945 | Cohn | 530/382 |
| 2,955,074 | 10/1960 | Hink | 424/147 |
| 3,959,249 | 5/1976 | Antonini | 530/394 |
| 4,318,902 | 3/1982 | Stephan | 530/388 |
| 4,440,679 | 4/1984 | Fernandes et al. | 530/394 |
| 4,560,655 | 12/1985 | Baker | 435/240.31 |
| 4,623,717 | 11/1986 | Fernandes et al. | 514/8 |

OTHER PUBLICATIONS

Islove et al., J. Exp. Med., 923-33 (1978), vol. 147.
Bidwell et al., pp. 257-300 in "Human Blood Coagulation, Hemeostasis and Thrombosis," 2nd Ed., Biggs(Ed) (1976).
Cook et al., Analytical Biochemistry, 149, 349-53, 1985.

Primary Examiner—Howard E. Schain
Assistant Examiner—Jeff P. Kushan
Attorney, Agent, or Firm—David J. Aston; Pamela A. Simonton

[57] ABSTRACT

Method and composition for providing a non-toxic, sterile, virally inactivated human transferrin preparation for use in cell culture systems. The method comprises saturation of the transferrin with an excess of iron, removal of free iron radicals and unwanted proteins, and pasteurization of the iron-bound transferrin substantially free of iron radicals.

10 Claims, No Drawings

VIRALLY INACTIVATED, NON-TOXIC, HUMAN TRANSFERRIN PREPARATION

BACKGROUND OF THE INVENTION

1. Field

This disclosure is concerned generally with an improved transferrin preparation and specifically with a method and composition comprising a virally inactivated, non-toxic transferrin preparation for use in cell culture systems.

2. Prior Art

Transferrins are iron-binding glycoproteins having molecular weights of 76,000–81,000. Serum transferrin is also referred to as $B_1$-metal combining protein or siderophilin. Transferrin is well know as an important, if not essential, supplement to serum-free media. Although the function of transferrin has yet to be resolved, it is believed to act as a growth factor, to provide cells with iron and to detoxify media by binding contaminating metal ions. These theories have been proposed by J. Kovar and F. Franek in "Hybridoma Cultivation in Defined Serum-Free Media:Growth-Supporting Substances", I. Transferrin, Folia Biol (Praha):31 (2):167–75, 1985.

Bovine and human transferrin products are available commercially. Suppliers include Miles Diagnostics, Kankakee, Ill.; Leon Laboratories, Ft. Lauderdale, Fla.; and Boehringer Mannheim Biochemicals, Indiana.

Presently, bovine transferrin is the prior art transferrin of choice since bovine are not susceptible to human viral contamination such as hepatitis and HIV. A drawback to using bovine transferrin in cell culture systems in the problem of species antigenicity. This is an even bigger drawback when the end product will be introduced into humans.

The prior art human transferrin products available are not viral-inactivated nor are they non-toxic to the cell culture systems.

U.S. Pat. No. 2,955,074 relates to a method of virally inactivating iron-binding glycoproteins and then removing the bound iron so that radioactive isotopes can be bound to the transferrin. The bound iron is removed by a chelating agent. This method was also used by H. G. Wada, P. E. Hass, and H. H. Sussman, in "Transferrin Receptor in Human Placental Brush Border Membranes", J. Biol. Chem., Vol. 254, No. 24, pp. 12,629–12,635, 1979. The method of U.S. Pat. No. 2,955,074 and of Wada, teach processing the transferrin after pasteurization which can result in contamination of the transferrin preparation with viral and microbial contaminants.

SUMMARY OF THE INVENTION

The invention provides a sterile, non-toxic, virally inactivated human transferrin preparation for use in cell culture systems that does not have the drawback of antigenicity, associated with bovine transferrin, or the drawback of the risk of disease syndrome, associated with human proteins that have not been pasteurized. The method comprises the saturation of transferrin with an excess of iron followed by the separation of the non-bound, iron radicals and unwanted proteins. This preparation is then pasteurized for about 10 hours at 60° C. and has been found to be non-toxic in cell culture systems.

DETAILED DESCRIPTION OF THE INVENTION

The starting material for the method and composition of the invention is purified, iron-binding glycoprotein (transferrin). One method of obtaining purified, iron-binding transferrin is fractionation of blood plasma according to the Cohn ethanol fractionation technique or its modifications. [see for example, Cohn et al, J. Chem. Soc. 68, 459 (1946); Oncley et al, ibid., 71, 541 (1949); U.S. Pat. No. 2,390,074; "The Plasma Proteins", 2nd ed., Volume III, pages 548–550, Academic Press, New York, NY]to give a Cohn fraction containing transferrin. An aqueous solution of transferrin containing Cohn fraction is prepared, and the pH of the solution is adjusted to about 5.5. A polycondensed polyglycol, for example 5% polyethylene glycol (PEG) is added to the solution, the pH of which is then adjusted to about 5.5 to selectively precipitate unwanted proteins from the effluent in which a substantial preparation of the transferrin is retained. A poly condensed polyglycol, for example 10% polyethylene glycol (PEG) is added to the remaining solution containing the transferrin at a pH range of 5.5 and a temperature range of about 5 to about 10° C. to selectively precipitate the transferrin. The selected example is not meant to be limiting. An increase in pH requires a concomitant increase in the percent PEG. For example, at pH 7.5 the percent PEG was increased from 10% to 25%.

The precipitated transferrin is dissolved in a physiologically acceptable buffer, such as Tris or phosphate and the pH adjusted to a range of about 7.5 to about 8.0. Ferrous ammonium sulfate or any other approximately neutral ferrous or ferric salt is dissolved in the buffered solution in the proportion of from 0.8 to 1.8 milligrams of iron per gram of transferrin. The solution is allowed to react for about 12–18 hours to obtain a >90% iron-bound transferrin. The solution is then filtered to remove substantially all of the free iron radicals as an insoluble phosphate salt. The iron-bound transferrin, substantially free of non-bound iron radicals is separated from other unwanted proteins such as albumin, haptoglobin, hemopectin and ceruloplasmin by DEAE ion exchange chromatography and then pasteurized at about 60° C. for about 10 hours. The pasteurization can take place batchwise but preferably the product is pasteurized in its final container.

SPECIFIC EMBODIMENTS

As demonstrated in Table I, a volume of Cohn Fraction IV-4 was dissolved in 9–10 volumes of 0.01 M $PO_4^{-3}$ buffer. A 5% solution of $PEG_{4000}$ was added. The pH was adjusted to 5.5 and temperature was maintained between 5° C. to 10° C., preferably at 5° C. The solution was allowed to react, and the precipitate containing unwanted proteins, such as IgG, IgM, etc., was discarded. A 10% solution of $PEG_{4000}$ was added to the supernatant. The pH was adjusted to 5.5, and the temperature maintained at 5° C. The supernatant was discarded and the resulting precipitate was dissolved in 0.001 M $PO_4^{-3}$. Ferrous ammonium sulfate was added in a ratio of at least 1.3 mg of $Fe^{+2}$ to gram of protein. The pH was adjusted to 7.5 and allowed to react for 12–18 hours. The solution was then filtered to remove any $Fe_3(PO_4)_2$. The resulting supernatant was contacted with a DEAE-Sepharose column. The column was washed with 0.01–0.15 M $PO_4^{-3}$ at a pH of 7.5. The iron-bound transferrin was eluted from the column with 0.05 M $PO_4^{-3}$ at 7.5. The resulting iron-bound transferrin solution was then passed through a sterile filter into final containers. The filled containers were pasteurized at 60° C. for 10 hours.

TABLE I

| COHN FRACTION IV-4 | |
|---|---|
| Dissolve in 9 vol. of 0.01 M $PO_4^{-3}$ pH 5.5 Temp = 5 to 10° C. $PEG_{4000}$ = 5% | Buffer |
| | pH 5.5 Temp = 5° C. $PEG_{4000}$ = 10% |
| Precipitate (Discard) (IgG, etc.) | |
| Precipitate | Supernatant (Discard) |
| Dissolve in 0.001 M $PO_4^{-3}$ pH 7.5 $Fe^{+2}$ 1.3 mg/gm Protein React 12-18 hours Filter | |
| $Fe_3(PO_4)_2$ | Add to DEAE-Sepharose Wash w/0.01 M $PO_4^{-3}$ @ pH 7.5 Elute w/0.05 $PO_4^{-3}$ @ pH 7.5 Sterile Filter Fill, Pasteurize |

The non-toxic, sterile, virally inactivated transferrin preparation of this disclosure is useful for cell culture systems for the preparation of injectables using new technologies including recombinant DNA and monoclonal antibodies.

Given the above disclosure, it is thought variations will occur to those skilled in the art. Accordingly, it is intended that the above example should be construed as illustrative and the scope of the invention should be limited only by the following claims.

We claim:

1. A method of preparing a sterile, virally inactivated, human, non-toxic, stable transferrin preparation, comprising of steps of
   (a) fractionating human plasma to obtain partially purified transferrin solution;
   (b) adding a soluble iron salt to the solution of Step (a) in the proportion of at least 1.3 milligrams of iron per gram of transferrin;
   (c) reacting said iron salt with said transferrin to form a saturated transferrin-iron complex and removing the non-complexed iron from the solution;
   (d) separating non-transferrin proteins from the solution of step (c); and
   (e) heating the iron-containing transferrin obtained in step (d) in order to inactivate viruses.

2. The method of claim 1 wherein in step (c) the non-bound iron is removed by precipitation of iron.

3. The method of claim 2 wherein the non-bound iron is precipitated as an insoluble phosphate salt.

4. The method of claim 1 wherein the proteins recited in step (d) are removed by contacting the solution of step (d) with an anion exchange column.

5. The method of claim 4 wherein said anion exchange column is DEAE-Sapharose washed with about 0.01 to about 0.15 M $PO_4^{-3}$ at a pH of about 7.5 and the iron-containing, iron-binding glycoprotein is eluted with about 0.05 M $PO_4^{-3}$ at a pH of about 7.5.

6. The method of claim 1 wherein the solution of step (e) is pasteurized at a temperature of about 60° C. for about 10 hours.

7. The method of claim 1 wherein said step of fractionating human plasma comprises the preparation of a purified transferrin paste and further comprising the step of:
   dissolving said transferrin paste in a phosphate buffer solution and adding to the buffer solution said soluble iron salt.

8. The method of claim 1 further comprising:
   (f) adding sterilized transferrin to a cell culture system.

9. The method of claim 1 wherein said heating step of (e) is preceded by the step of sterile filtering said transferrin into final containers.

10. The method of claim 1 wherein the heating step of (e) is carried out with said transferrin in its final container.

* * * * *